United States Patent [19]

Barberet et al.

[11] Patent Number: Plant 7,177

[45] Date of Patent: Mar. 6, 1990

[54] CARNATION PLANT NAMED LONDILING

[75] Inventors: Nicole Barberet; Henri Blanc, both of Antibes, France; Antonio Di Giorgio; Renato Di Giorgio, both of San Remo, Italy

[73] Assignee: Establissements Barberet et Blanc, La Londe-Les-Maures, France

[21] Appl. No.: 315,022

[22] Filed: Feb. 24, 1989

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and distinct standard carnation variety distinguished particularly by its very large generally yellow blooms each of which comprises very many petals with a verigated yellowish and light red coloration whereby the flower in general has an overall verigated yellow red spotted appearance, the flowers being borne singly on long, strong stems of a plant having an average height of about 150 cm. at eight months of growth. This new plant also has a recurrent blooming habit producing flowers profusely during the Spring, Midseason and Fall flowering seasons with moderately abundant production of foliage.

1 Drawing Sheet

BACKGROUND OF THE NEW PLANT

This new carnation variety originated as a seedling of a hybrid developed by us in 1985 at the Di Giorgio Nursery at San Remo, Italy, by crossing two varieties selected by us from the Di Giorgio collection of carnations maintained at the Di Giorgio nursery for breeding purposes. This particular seedling was selected for propagation because of its very large blooms having a bright overall variegated mainly yellow coloration and propagation of the selected seedling was done under our direction by means of cuttings. Such propagation was carried on through several successive generations at San Remo which demonstrated conclusively that the novel characteristics of the selected seedling would remain true from generation to generation and appeared to be firmly affixed so that homogeneity for commercial production could be assured. The flowers of this new variety are borne singly on long, strong, upright stems of a very tall plant having excellent characteristics for commercial propagation for cut flower production.

Our new carnation variety is now being propagated for commercial purposes by means of cuttings, as well as by in vitro propagation procedures, at Establissements Barberet et Blanc, Laboratoire de Physiologie Vegetalle, 83250 La Londe-Les Maures, France.

DESCRIPTION OF THE DRAWING

Our new standard carnation variety is illustrated by the accompanying photographic drawing which shows several stems with flowers in various stages of development, one stem having a bud at a stage shortly after dividing of the sepals for opening of the full blossom, the color rendition being as nearly true to that herein specified as is reasonably possible to obtain by professional photographic procedures.

DESCRIPTION OF THE NEW PLANT

The following is a detailed description of our new carnation variety based upon observation of plants grown in greenhouse, as well as outside, at San Remo, Italy in the Spring of 1988, the color designations stated herein being according to The R.H.S. Colour Chart published by The Royal Horticultural Society of London, England.

THE PLANT

Origin: Seedling.

Parentage:

*Seed parent.*—Variety No. 60.

*Pollen parent.*—Variety No. 689.

Each of these varieties is unnamed and unpatented and is identified in breeding records maintained at the Di Giorgio nursery office at Via Villetta 41, 18038 San Remo, Italy.

Classification:

*Botanic.*—*Dianthus caryophyllus.*

*Commercial.*—Standard Carnation.

Form: An erect bush having at least four stems emitted near the ground.

Height: Averages about 150 cm. at eight months of growth.

Main stem length: Less than 15 cm. due to pinching for branch production.

Branching: This plant is well branched.

Growth: Vigorous, upright and rigid.

Foliage:

*Quantity.*—Moderately abundant.

*Number of leaves.*—More than 120.

*Leaf size.*—(At the seventh node) Averages about 13.1 cm. long and about 1.1 cm. wide.

*Leaf shape.*—Oblong — with upwardly rolled and entire margins.

*Texture.*—Leathery.

*Color.*—Both upper and under sides, 189-A/B.

THE BUD

Size: Large.

*Diameter.*—Averages about 2.5 cm.

*Length.*—Averages about 3.5 cm.

Shape: Generally ovoid.

Rate of opening: Normal.

Color of petals: When sepals first divide, and when petals begin to unfurl, the color is the same as at full bloom.

Sepals:

*Number.*—Five.

*Shape.*—Generally ovate, with acuminate tip and joined together at the lower parts.

*Character.*—The sepals are hooded over the bud before dividing and curl back when the flower opens.

*Color.*—Inside 145-D. Outside, 137-C and 145-A.

*Striae.*—Longitudinal.

Calyx:

*Shape.*—Funnel-shaped and broad.

*Aspect.*—Smooth.

*Splitting.*—Sometimes a little splitting occurs.

Flower stem:

*Length.*—Averages about 83 cm. (cut at the tenth node).

*Color.*—189-A/B.

*Character.*—Erict and rigid.

THE FLOWER

Blooming habit: Recurrent, blooming profusely during the Spring, Midseason and Fall blooming seasons, with a tendency to give new blooms in the Fall.

Size of flower: Very large.

*Diameter.*—Averages about 8.8 cm.

*Depth.*—Averages about 5.7 cm.

Borne: Singly on a long, strong, upright stem.

Shape: When bloom first opens, high-centered. When bloom matures, dome-shaped.

Petalage:

*Number of petals.*—Averages about eighty-two.

*Arrangement.*—Imbricated.

*Form.*—Fan-shaped and a little serrated at the outer edges.

*Texture.*—Leathery.

*Aspect.*—Satiny.

*Color.*—Both inner and outer petals: Varigation of Yellow 2-C, 3-C, and Carmine and Carmine Rose 52-B, 52-C and 155-B. Base — Greenish.

*Petaloids.*—Number: Less than sixteen. Size: Smaller than the petals. Color: The same as the petals.

Flower stem:

*Character.*—Upright with good strength with outwardly curved foliage.

Discoloration after full bloom: Very little.

Persistence: The flowers hang on and dry.

Fragrance: Perceptible.

Lasting quality: As a cut flower, at least ten days in vase keeping.

REPRODUCTIVE ORGANS

Stamens:

*Number.*—Four to eight.

*Arrangement.*—Around the ovary.

*Anthers.*—Size: Less than 4 mm. Color: Yellowish.

*Filaments.*—Length: Averages about 3.7 cm. Color: Yellowish.

Pistils:

*Number.*—Three.

*Styles.*—Length: About 3.7 cm. Color: Yellowish.

*Stigma.*—Color: Yellowish.

Character of ovaries: Ribbed.

This new variety most nearly resembles the variety Londorga U.S. Plant Pat. No. 5,784. Compared to Londorga, however, this new variety differs by having little striae in the flower petals.

We claim:

1. The new and distinct standard carnation variety substantially as herein shown and described, particularly characterized by the very large size of its blooms and the varigated yellow color of the flower petals which provide a generally overall yellow varigated appearance.

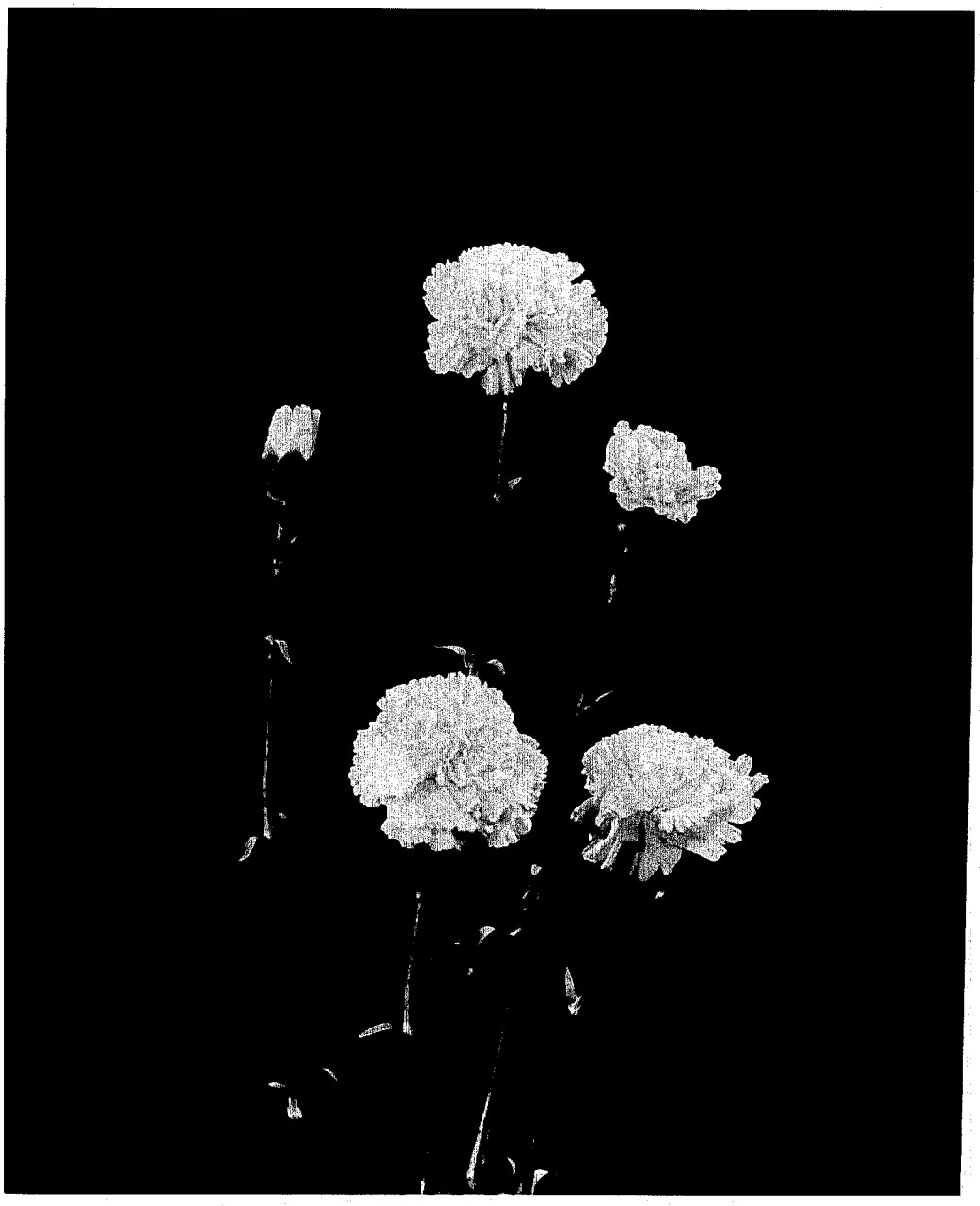

* * * * *